United States Patent [19]

Gilbert

[11] 4,147,883
[45] Apr. 3, 1979

[54] CONVERSION OF CYCLOALKYLHYDROPEROXIDES TO ALKANE DICARBOXYLIC ACIDS

[75] Inventor: Arthur H. Gilbert, Middlesbrough, England

[73] Assignee: Imperial Chemical Industries Limited, London, England

[21] Appl. No.: 708,737

[22] Filed: Jul. 26, 1976

[30] Foreign Application Priority Data

Sep. 1, 1975 [GB] United Kingdom ............... 35946/75

[51] Int. Cl.² ..................... C07C 51/24; C07C 55/14
[52] U.S. Cl. ................................................ 562/523

[58] Field of Search .................... 260/537 P; 562/523

[56] References Cited

U.S. PATENT DOCUMENTS

| 2,298,387 | 10/1942 | Kenyon et al. | ................. 260/537 P |
| 2,851,496 | 9/1958 | Cates, Jr. et al. | ................. 260/537 P |

*Primary Examiner*—Vivian Garner
*Attorney, Agent, or Firm*—Cushman, Darby & Cushman

[57] ABSTRACT

A cycloalkylhydroperoxide is converted to an alkanedicarboxylic acid of the same number of carbon atoms, e.g. cyclohexylhydroperoxide to adipic acid, by reaction with nitrogen dioxide.

6 Claims, No Drawings

CONVERSION OF CYCLOALKYLHYDROPEROXIDES TO ALKANE DICARBOXYLIC ACIDS

This invention relates to the conversion of organic hydroperoxides to carboxylic acids and more particularly to the conversion of cycloalkylhydroperoxides to alkanedicarboxylic acids.

The invention provides a process for the conversion of a cycloalkylhydroperoxide to an alkanedicarboxylic acid having the same number of carbon atoms by treating it with nitrogen dioxide.

The term nitrogen dioxide includes any present in dimeric form, that is as dinitrogen tetroxide.

As cycloalkylhydroperoxide there may be used cyclopentylhydroperoxide, cyclododecylhydroperoxide and especially cyclohexylhydroperoxide.

Cyclohexylhydroperoxide may be obtained, for example, by oxidising cyclohexane in the liquid phase with air or other oxygen-containing gas in the absence of a catalyst and preferably at a low conversion of cyclohexane, for example less than 5% conversion. The product, consisting of a solution in cyclohexane of cyclohexylhydroperoxide, and also, usually, of smaller amounts of cyclohexanol and cyclohexanone, may be concentrated by distilling off some of the cyclohexane to give a more concentrated solution of cyclohexylhydroperoxide for example a solution containing from 10% to 20% by weight of the hydroperoxide. Such a solution is very suitable for conversion of cyclohexylhydroperoxide to adipic acid. It is an advantage of the process of our invention that the cycloalkylhydroperoxide can be reacted in solution in the hydrocarbon from which it is derived, and that it is unnecessary first to isolate such a rather unstable material.

In the treatment of the cycloalkylhydroperoxide with nitrogen dioxide according to our invention, the nitrogen dioxide is preferably added in the gaseous or liquid phase to the cycloalkylhydroperoxide in the liquid phase, preferably in solution in a hydrocarbon solvent and conveniently in solution in the cycloalkane from which the hydroperoxide is derived by oxidation. The temperature of the treatment is preferably from 5° to 100° C. The pressure may be atmospheric or, if necessary, above atmospheric in order to keep the reactants and solvent in the liquid phase. The nitrogen dioxide, if gaseous, may be diluted with other gases inert in the reaction, for example nitrous oxide or nitrogen; and may be used in solution, for example in a hydrocarbon solvent such as cycloalkane from which the hydroperoxide is derived. The reaction may be complete in times varying from a few minutes, for example 5 minutes, up to many hours, for example 30 hours. The alkanedicarboxylic acid product of the reaction separates as a solid from the liquid phase and may be isolated by filtration or centrifuging. The process may readily be adapted to continuous operation.

U.S. Pat. No. 2,298,387 describes a process for the production of acids by the treatment of alcohols, aldehydes or ketones with nitrogen dioxide, for example of adipic acid by such treatment of cyclohexanol or cyclohexanone.

It is an advantage of our process for converting cycloalkylhydroperoxides to alkanedicarboxylic acids having the same number of carbon atoms that the proportion of by-product alkanedicarboxylic acids having a lower number of carbon atoms, for example glutaric acid and succinic acid in the case of cyclohexylhydroperoxide, is conspicuously low.

The invention is illustrated but not limited by the following Examples.

EXAMPLE 1

Into 66.2 g. of a solution in cyclohexane of 0.071 g. moles of cyclohexylhydroperoxide, 0.032 g. moles of cyclohexanone and 0.010 g. moles of cyclohexanol at 20° C. nitrogen dioxide was passed at a steady rate. After 10 minutes an exothermic reaction ensued and the temperature was controlled at 50° ± 5° C. for 1 hour after which the exotherm ceased. The temperature was kept at 45° C. for a further 1 hour and the passage of nitrogen dioxide then discontinued. The mixture was then stirred for 16 hours at 20° C., then heated to 70° C. for 2 hours and cooled again. The solid was filtered off and dried (17.01 g.). Analysis by gas-liquid chromatography showed the solid to contain 67.4% by weight of adipic acid, 5.3% of glutaric acid, 3.8% of succinic acid and 5.1% of hydroxycaproic acid.

EXAMPLE 2

Into 81.9 g. of a solution in cyclohexane of 0.088 g. moles of cyclohexylhydroperoxide, 0.040 g. moles cyclohexanone and 0.012 g.moles cyclohexanol at 20° was added liquid nitrogen dioxide at a steady dropwise rate while stirring at 600 rpm. An exothermic reaction ensued but the temperature was kept below 25° by cooling. After 95 mins. The exothermic reaction had ceased and addition of nitrogen dioxide was discontinued. After a further 20 hrs. stirring at room temperature the solid was filtered, washed with cyclohexane and dried (22.4 g.). Analysis by gas-liquid chromatography showed the solid to contain 69% adipic acid, 4.3% glutaric acid, 3.3% succinic acid and 5.7% of hydroxycaproic acid. The filtrate was found to contain 0.0084 g.moles of cyclohexylnitrate.

I claim:

1. A process for the conversion of a cycloalkylhydroperoxide dissolved in a cycloalkane to an alkane dicarboxylic acid having the same number of carbon atoms, said cycloalkylhydroperoxide formed by oxidizing said cycloalkane, comprising:
    treating said cycloalkylhydroperoxide with nitrogen dioxide at a temperature in the range from 5° to 100° C. to form an alkane dicarboxylic acid having the same number of carbon atoms as said cycloalkylhydroperoxide.

2. The process of claim 1 in which the nitrogen dioxide is added in the gaseous or liquid phase to the cycloalkylhydroperoxide in the liquid phase.

3. The process of claim 2 in which cyclohexylhydroperoxide is converted to adipic acid in solution in cyclohexane.

4. The process of claim 3 for the manufacture of adipic acid which comprises treating a solution of cyclohexylhydroperoxide in cyclohexane with nitrogen dioxide at a temperature in the range 5° to 100° C. and separating solid adipic acid from the liquid cyclohexane.

5. The process of claim 3 in which a solution of 10% to 20% by weight of cyclohexylhydroperoxide in cyclohexane is used.

6. The process of claim 5 in which the solution of cyclohexylhydroperoxide in cyclohexane is the product of a liquid phase oxidation of cyclohexane with an oxygen-containing gas in the absence of a catalyst.

* * * * *